US009730922B2

(12) United States Patent
Maiuri et al.

(10) Patent No.: US 9,730,922 B2
(45) Date of Patent: *Aug. 15, 2017

(54) COMBINED THERAPY FOR CYSTIC FIBROSIS

(71) Applicant: I.E.R.F.C. EUROPEAN INSTITUTE FOR CYSTIC FIBROSIS RESEARCH, Milan (IT)

(72) Inventors: Luigi Maiuri, Milan (IT); Valeria Raia, Milan (IT); Fabio Borella, Milan (IT); Guido Kroemer, Milan (IT)

(73) Assignee: I.E.R.F.C. Europ. Inst. for Cystic. Fibrosis Res., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/817,232

(22) Filed: Aug. 4, 2015

(65) Prior Publication Data

US 2015/0328203 A1 Nov. 19, 2015

Related U.S. Application Data

(63) Continuation of application No. 13/895,741, filed on May 16, 2013, now Pat. No. 9,132,123.

(30) Foreign Application Priority Data

May 17, 2012 (EP) .................................... 12168409

(51) Int. Cl.
| | |
|---|---|
| *A61K 31/47* | (2006.01) |
| *A61K 31/145* | (2006.01) |
| *A61K 31/352* | (2006.01) |
| *A61K 31/047* | (2006.01) |
| *A61K 31/05* | (2006.01) |
| *A61K 31/13* | (2006.01) |
| *A61K 31/192* | (2006.01) |
| *A61K 31/198* | (2006.01) |
| *A61K 31/357* | (2006.01) |
| *A61K 31/37* | (2006.01) |
| *A61K 31/7034* | (2006.01) |
| *A61K 45/06* | (2006.01) |
| *A61K 31/366* | (2006.01) |

(52) U.S. Cl.
CPC ............ *A61K 31/47* (2013.01); *A61K 31/047* (2013.01); *A61K 31/05* (2013.01); *A61K 31/13* (2013.01); *A61K 31/145* (2013.01); *A61K 31/192* (2013.01); *A61K 31/198* (2013.01); *A61K 31/352* (2013.01); *A61K 31/357* (2013.01); *A61K 31/366* (2013.01); *A61K 31/37* (2013.01); *A61K 31/7034* (2013.01); *A61K 45/06* (2013.01)

(58) Field of Classification Search
CPC ..... A61K 31/47; A61K 31/145; A61K 31/352

USPC ............................................ 514/1.8, 25, 312
See application file for complete search history.

(56) References Cited

U.S. PATENT DOCUMENTS

| | | | |
|---|---|---|---|
| 7,335,683 B2 | 2/2008 | Fischer et al. | |
| 9,132,123 B2* | 9/2015 | Maiuri ................. | A61K 31/047 |
| 2002/0115619 A1 | 8/2002 | Rubenstein et al. | |

FOREIGN PATENT DOCUMENTS

WO 2009/105234 8/2009

OTHER PUBLICATIONS

Luciani et al. SUMOylation of Tissue Transglutaminase as Link between Oxidative Stress and Inflammation. J Immunol 183:2775-2784, 2009.*
C. Andersson, et al., Activation of F508 CFTR in a Cystic Fibrosis . . . , Eur. Respir., J., vol. 15, pp. 937-941, 2000.
Fredrick Van Goor, et al., Rescue of CF Airway Epithelial Cell . . . , PNAS, vol. 106, No. 44. pp. 18825-18830, 2009.
Alessandro Luciani, et al., Defective CFTR Induces Aggresome Formation and Lung . . . , Nature Cell Biology, vol. 12, No. 9, 2010.
Ji-Eun Kim, et al., Adiponectin Inhibits Palmitate-Induced Apoptosis Through Suppression . . . , Journal of Endocrinology, vol. 207. pp. 35-44, 2010.
Avik Roy, et al., Sodium Phenylbutyrate Controls Neuroinflammatory . . . , PLOS ONE, vol. 7, 2012.
Mairead Kelly-Aubert, et al., GSH Monoethyl Ester Rescues Mitochondrial . . . , Human Molecular Genetics, vol. 20, No. 14, pp. 2745-2759, 2011.
Wenbo Zhou, et al., Phenylbutyrate Up-Regulates the DJ-1 . . . , Journal of Biological Chemistry, vol. 286, No. 17, 2011.
Karen T. Chang, et al., Regulation of Lifespan by Histone Deacetylase, Ageing Research Reviews, vol. 1, pp. 313-326, 2002.
Sonemany Salinthone, et al., Lipoic Acid Attenuates Inflammation . . . , PLOS ONE, vol. 5, No. 9, 2010.
Hyung-Lyun Kang, et al., Life Extension in *Drosophila* by Feeding a Drug, PNAS, vol. 99, No. 2, pp. 838-843, 2002.
Nicoletta Pedemonte, et al., Phenylglycine and Sulfonamide Correctors . . . , Mol. Pharmacol, vol. 67, No. 5, pp. 1797-1807, 2005.
Francesco Galli, et al., Oxidative Stress and Antioxidant . . . , Biochimica et Biophysica Acta, vol. 1822, pp. 690-713, 2012.
Yih-Lin Chung, et al., Epigenetic Therapy Using the Histone Deacetylase . . . , Carcinogenesis, vol. 30, No. 8, pp. 1387-1397, 2009.
European Search Report in counterpart EP12168409.6, Sep. 2012.

* cited by examiner

*Primary Examiner* — Clinton Brooks
*Assistant Examiner* — Yih-Horng Shiao
(74) *Attorney, Agent, or Firm* — Silvia Salvadori, P.C.; Silvia Salvadori (57) ABSTRACT

There is disclosed a combination of inhibitors of Tissue Transglutaminase (TG2), inhibitors of reactive oxygen species (ROS) and CFTR channel activators (potentiators) for separate, sequential or simultaneous administration to CF patients carrying the ΔF508-CFTR mutation, and pharmaceutical compositions thereof.

19 Claims, 3 Drawing Sheets

```
SEQUENCE LISTING

<160> NUMBER OF SEQ ID NOS: 2

<210> SEQ ID NO 1
<211> LENGTH: 20
<212> TYPE: DNA
<213> ORGANISM: Unknown
<220> FEATURE:
<223> OTHER INFORMATION: artificial primer

<400> SEQUENCE: 1
ccaccacgct cttctgtcta                                              20

<210> SEQ ID NO 2
<211> LENGTH: 20
<212> TYPE: DNA
<213> ORGANISM: Unknown
<220> FEATURE:
<223> OTHER INFORMATION: artificial primer

<400> SEQUENCE: 2
agggtctggg ccatagaact                                              20
```

COMBINED THERAPY FOR CYSTIC FIBROSIS

This non-provisional patent application is a continuation application of U.S. patent application Ser. No. 13/895,741 filed on May 16, 2013, which claims priority to and benefit of European Patent Application No. 12168409.6 filed on May 17, 2012 the content of which are incorporate by reference in their entirety.

The present invention relates to the treatment of Cystic Fibrosis (CF) in patients carrying the ΔF508-CFTR mutation. More specifically the invention provides a combination of inhibitors of Tissue Transglutaminase (TG2), inhibitors of reactive oxygen species (ROS) and CFTR channel activators (potentiators) for separate, sequential or simultaneous administration to CF patients carrying the ΔF508-CFTR mutation. Another object of the invention is a pharmaceutical composition containing the TG2 inhibitor, the ROS inhibitor and/or the potentiator for use in this therapeutical method.

BACKGROUND OF THE INVENTION

CF is an autosomal recessive disorder, the most common lethal genetic disease in Caucasians, (O'Sullivan 2009; Rowe, 2005; Accurso, 2006) characterized by chronic lung disease, the main cause of morbidity and mortality, pancreatic dysfunction, raised electrolyte levels in sweat, and male infertility. CF is caused by mutations of one single protein, the cystic fibrosis transmembrane conductance regulator (CFTR), a cAMP—regulated chloride channel that is primarily located at the apical membrane of epithelial cells (Park 2010). More than 1500 different disease-associated mutations have been identified, some of them encoding CFTR mutants reaching the cell plasma membrane but lacking CFTR activity, other ones encoding negligible amounts of protein or misfolded mutants that are prematurely degraded and fail to reach a cell surface localization. Among the latter, a single codon deletion, ΔF508, occurs in about 90% of CF patients on at least one allele. Due to its misfold, ΔF508-CFTR loses its essential ion channel activity at the plasma membrane (PM), thus provoking local inflammation, increased susceptibility to respiratory bacterial infections, and progressive pulmonary and digestive insufficiency (Collins 1992).

A still partially functional ΔF508-CFTR can be rescued at the plasma membrane (PM) by molecules that correct ΔF508-CFTR intracellular retention and degradation (correctors). However, ΔF508-CFTR that reaches the PM is unstable as result of a [carboxyl-terminus heat shock cognate 70 (Hsc70)-interacting protein] (CHIP)-mediated ubiquitination, followed by redirection of the protein from endosomal recycling towards lysosomal delivery and degradation (Okiyoneda T, 2010). Therefore, CF patients carrying the misfolded ΔF508-CFTR are poorly responsive to potentiators of CFTR channel activity that can be used for the treatment of the small subset of CF patients that carry PM-resident CFTR mutants (Ramsey B W, 2011; Davids P B, 2011). Therefore, fixing the misfolded ΔF508-CFTR mutant at the PM after rescue is the principal objective of "CFTR-repairing" therapies (Lucaks G L, 2012; Davids P B, 2011).

An ideal therapy for CF should aim not only at rescuing CFTR function, but also at ameliorating chronic lung inflammation and the increased susceptibility to bacterial infections that constitute the main clinical problem of CF patients (Belcher C N, 2010). A recent clinical trial with the CFTR corrector VX-809 in ΔF508-CFTR homozygous patients demonstrated modest dose-dependent reductions in sweat chloride (Clancy J P 2012; Elborn S. 2012). However, no improvement in lung function or CF complications was reported (Clancy J P 2012; Elborn S. 2012), and Phase II clinical studies combining VX-809 and the potentiator VX-770 have to be awaited to evaluate their clinical benefit.

We have reported that a complex derangement of protein homeostasis (proteostasis) occurs in CF epithelial cells and is caused by the loss of CFTR function. Increased levels of reactive oxygen species (ROS) induced by defective CFTR function lead to tissue transglutaminase (TG2) activation driving cross-linking and aggresome accumulation of several TG2-substrate proteins (Maiuri L, 2008; Luciani A, 2009), among which the sequestration of the essential autophagy protein Beclin-1 (Luciani A, 2010; Luciani A, 2011). The functional sequestration of Beclin 1 disloges the PI3K complex III away from the endoplasmic reticulum (ER), thus inhibiting autophagosome formation and driving inflammation in CF airways. This generates a feed forward loop that sustains oxidative stress and perpetrates inflammation. Defective autophagy was also confirmed in CF macrophages (Abdulrahman B A, 2012). Rescuing Beclin-1 and autophagy either by transfection-enforced Beclin 1 overexpression or by means of TG2 inhibitors (e.g. cystamine) or antioxidants (e.g. N-acetyl-cysteine or the superoxide dismutase (SOD)/catalase-mimetic EUK-134), blunts inflammation in ΔF508-CFTR homozygous airways, both in mice in vivo and in human tissues, in vitro (Luciani A, 2010; Luciani A, 2011). Moreover, rescuing autophagy favors ΔF508-CFTR trafficking to the plasma membrane of the epithelial cells.

DESCRIPTION OF THE INVENTION

Using different in-vitro, ex vivo and in-vivo experimental models of ΔF508-CFTR cystic fibrosis, it was surprisingly found that pre-treatment with either a TG2-inhibitor or an agent inhibiting reactive oxygen species (ROS inhibitor) or a combination thereof, enables the action of CFTR potentiators on ΔF508-CFTR well beyond withdrawal of the TG2 inhibitor and/or of the ROS inhibitor, thereby enabling for the first time an effective and long-lasting therapeutic approach to cystic fibrosis caused by ΔF508-CFTR mutation.

It was first established an ex-vivo experimental setting where primary nasal epithelial cells freshly obtained by nasal brushing from ΔF508-CFTR homozygous patients were incubated for 18 hrs with either cystamine or EUK-134 or with the well known CFTR correctors Corr-4a and VRT-325 (Varga K, 2008) followed by wash and re-culture for 24 hrs with medium. At the end of incubation it was assessed CFTR channel function by a standardized procedure of assessment of iodide efflux (Silvis M R 2009). Surprisingly it was found that cystamine and EUK-134, were effective not only to rescue ΔF508-CFTR function, but also, unlike Corr-4a and VRT-325, to render the cells capable of conserving ΔF508-CFTR response to CFTR potentiators genistein, VX-532 well beyond drug washout. Therefore, it is provided the unpredictable evidence that CFTR potentiators can turn out effective on ΔF508-CFTR in human CF airway epithelial cells if the environment has been previously restored by proteostasis regulators as cystamine or EUK-134.

It was used another human ex vivo experimental setting where nasal polyp biopsies were obtained from ΔF508-CFTR homozygous patients, as idiopatic non-allergic nasal polyposis often complicate CF. ΔF508-CFTR homozygous nasal polyp biopsies were treated with cystamine for 18 hrs, washed and then cultured for further 36 hrs in the absence of cystamine. Surprisingly, in this experimental model, the nearest to in vivo situation, as different cell types may interact with the neighbouring cells within their natural environment, the reduction of signs of mucosal inflammation coupled with a conserved CFTR expression at the epithelial surface, persisted for 36 hrs after cystamine withdrawal. Moreover, in this setting, an extended experimental procedure consisting of a single short pulse of biopsies with the above mentioned CFTR potentiators at the end of washout period, significantly increased the effects of cystamine in damping down mucosal inflammation while CFTR potentiators were totally uneffective on biopsies that were not pre-treated with cystamnine. These results demonstrate a synergistic effect of sequential treatment of cystamine plus genistein and provide the unexpected evidence that CFTR potentiators are beneficial in ΔF508-CFTR airways provided that the ΔF508-CFTR is firstly stabilized at the plasma membrane of airway epithelial cells by pre-treatment with cystamine.

To prove the efficacy of such a sequential drug administration on ΔF508-CFTR in vivo, it was used another experimental setting where mice homozygous for the ΔF508-CFTR (Cftr$^{F508del}$) were administered intraperitoneally for 7 days with vehicle alone or with the TG2 inhibitor cystamine. The latter proved able in vitro and in ex vivo human CF airway samples to prolong the expression of ΔF508-CFTR at the epithelial surface beyond drug washout. In this experimental model, the effects of cystamine in sustaining relocation of ΔF508 protein at the lung epithelial surface and in reducing lung inflammation persisted for 10 days after cystamine withdrawal. In an extended experimental setting where Cftr$^{F508del}$ mice were treated with daily inhalations of either intraperitoneal or aerosolized cystamine for one week, kept for another week without treatment and then sequentially pulsed with the potentiator genistein, the signs of lung inflammation, either constitutive or elicited by Lipopolisaccharide from Pseudomonas Aeruginosa (PA-LPS) were significantly reduced in cystamine-pretreated mice by the CFTR potentiator that, on the contrary, was uneffective in mice that had not received cystamine pre-treatment.

To provide the rationale for the use of either TG2 inhibitors or drugs that reduce ROS levels as pre-treatment before the administration of CFTR potentiators, another experimental setting was used, where airway epithelial cell lines carrying ΔF508/ΔF508 CFTR mutations were treated with cystamine or EUK-134 or where TG2 was depleted by a small interference RNA approach or where ROS were reduced by the overexpression of the human Manganese Superoxide-dismutase (Mn-SOD). In a first group of experiments, cells were pre-treated for 18 h with cystamine or EUK-134 and then kept in medium alone for further 48 h and finally pulsed with genistein or VX-532, as above indicated. In another experimental setting, TG2 gene silencing or Mn-SOD overexpression were performed instead of incubation with cystamine or EUK-134 and cells were analyzed after 48 h. The analysis of CFTR function after treatments revealed that either pharmacological pre-treatments or TG2 knock down or Mn-SOD overexpression were similarly effective in enabling the action of CFTR potentiators in stimulating CFTR channel function. These results demonstrate that the effects of cystamine and EUK-134 rely on their ability to inhibit TG2 activity and/or reduce ROS levels.

Another experimental approach was used to test the efficacy of other pharmacological agents able to damp down TG2 and/or reduce the levels of ROS. These pharmacological agents were molecules able to inhibit TG2 activity through different mechanisms, as previously described, (herein generally indicated as TG2 inhibitors) as thiol compounds which are preferably selected from the group consisting of cystamine, cysteamine, lipoic acid, tiopronin, acetylcysteine, carboxymethylcystein, erdosteine, moguisteine, mesna and glutathione (GSH). The ROS inhibitors preferably include phenols and polyphenols such as ellagic acid, caffeic acid, cumaric acid, gallic acid, resveratrol and carotenoids such as luthein, astaxhantin and zheaxhantin. These pharmacological agents were tested following the experimental approach of pre-treatment (18 h), washout (48 h) and single pulse with potentiators, in presence or absence of PA-LPS stimulation after pulse with potentiators, following the procedure above described. Using these experimental settings, it was found that the cysteamine, lipoic acid, tiopronin, acetylcysteine, carboxymethylcystein, erdosteine, moguisteine, mesna and glutathione (GSH), as well as the ellagic acid, caffeic acid, cumaric acid, gallic acid, resveratrol and carotenoids such as luthein, astaxhantin and zheaxhantin are endowed with similar effects as cystamine or EUK-134 in enabling the activity of CFTR potentiators genistein or VX-532 after washout, as described above. It was shown that all these tested substances were effective in reducing the levels of ROS and/or damping down TG2 protein and TG2 enzyme activity. It was also found that the pre-treatment with cystamine, EUK-134 as well as with the other pharmacological agents above mentioned, enables the activity of the CFTR potentiators genistein and VX-532 as well as of the well known CFTR potentiator VX-770 on ΔF508-CFTR 48 h after withdrawal of the molecules used as pre-treatment regimen.

Moreover, the efficacy of other molecules endowed with either ROS inhibiting activity or potentiator activity was tested. It was found that quercetin, silybin, apigenin, catechin, epigallocatechin, antocyanidins were as effective as genistein in stimulating CFTR function after pre-treatment with all the above mentioned molecules followed by 48 h of washout.

Altogether, these results support a novel approach for the treatment of F508-CFTR homozygous patients. Particularly these results indicate that the inhibition of TG2, as well as the reduction of ROS levels which sustain TG2 expression, induce and conserve ΔF508-CFTR protein at the epithelial surface after rescue thereby allowing potentiators to exert their activity of channel function enhancer on the ΔF508-CFTR still resident at the cell surface after drug suspension.

Accordingly, the present invention provides a combination of (i) a tissue transglutaminase TG2 inhibitor and/or (ii) an agent able to reduce the levels of reactive oxygen species (ROS inhibitor) and (iii) a channel activator (potentiator) of cystic fibrosis transmembrane conductance regulator (CFTR), for use in a method of treatment of a cystic fibrosis patient carrying the ΔF508-CFTR mutation, which comprises administering to said patient, the tissue transglutaminase TG2 inhibitor and/or the agent able to reduce the levels of ROS followed by the potentiator.

The agents generally generally indicated as TG2 inhibitors are thiol compounds which are preferably selected from the group consisting of cystamine, cysteamine, lipoic acid, tiopronin, acetylcysteine, carboxymethylcystein, erdosteine, moguisteine, mesna and glutathione (GSH). The TG2 inhibitor cystamine is particularly preferred.

The ROS inhibitors preferably include phenols and polyphenols such as ellagic acid, caffeic acid, cumaric acid, gallic acid, resveratrol and carotenoids such as luthein, astaxhantin and zheaxhantin.

Molecules that can be used as potentiators according to the present invention are disclosed in:

Davison H R et al, "Fluorinated DF508-CFTR correctors and potentiators for PET imaging, Bioorganic & Medicinal Chemistry Letters 22 (2012) 1602-1605;

Becq F et al, "Pharmacological therapy for cystic fibrosis: from bench to bedside", Journal of Cystic Fibrosis Volume 10 Suppl 2 (2011) S129-S145;

Moran O, "Model of the cAMP activation of chloride transport by CFTR channel and the mechanism of potentiators", Journal of Theoretical Biology 262 (2010) 73-79;

which are herein incorporated by reference in their entirety.

In a preferred embodiment, the potentiator is the compounds VX770 (Flume P A et al; for the VX08-770-104 Study Group. Ivacaftor in Subjects with Cystic Fibrosis who are Homozygous for the F508del-CFTR Mutation. Chest. 2012 Mar. 1).

Ramsey B W et al, VX08-770-102 Study Group A CFTR potentiator in patients with cystic fibrosis and the G551D mutation. N Engl J Med. 2011 Nov. 3; 365(18):1663-72;

Accurso F J et al, Effect of VX-770 in persons with cystic fibrosis and the G551D-CFTR mutation. N Engl J Med. 2010 Nov. 18; 363(21):1991-2003).

In an invention embodiment, the TG2 inhibitor and/or ROS inhibitor are administered to the patient for a period of 1 to 4 weeks, preferably for a period of 1 to 2 weeks.

At the end of said period of time, the administration of TG2 inhibitor and/or ROS inhibitor is stopped and the administration of potentiator is started and protracted.

In an alternative therapeutic regimen, the administration of TG2 inhibitor and/or ROS inhibitor is periodically resumed at intervals of 4 to 6 weeks during the administration of the potentiator, depending on the patient's response to the potentiator. In particular, the TG2-inhibitor and/or ROS inhibitor supply will become necessary whenever the effects of the potentiator therapy diminish and CF symptoms such as lung function significantly worsens or markers of inflammation, pancreatic dysfunction, or liver involvement as well as sweat electrolyte concentrations significantly increase. In this case, the administration of TG2 inhibitor and/or ROS inhibitor during potentiator therapy should last as long as necessary for patient's recovery from cystic fibrosis symptoms, generally for a period of 1 to 4 weeks.

The TG2 inhibitor, ROS inhibitor and the potentiator are preferably administered through the oral, respiratory or parenteral routes. Generally the pharmaceutical form and administration route will be determined on the basis of the specific molecule selected for therapy.

In another embodiment of invention, an agent possessing activity of either TG2 inhibitor or potentiator is co-administered with the TG2 inhibitor, the ROS inhibitor or with the potentiator. These agents are preferably flavonoids selected from quercetin, silybin, genistein, apigenin, catechin, epigallocatechin, antocyanidins.

The therapeutic treatment according to the present invention is conveniently administered to subjects diagnosed by genetic testing positive for ΔF508 mutations and positive sweat test, as well as to infants early diagnosed by newborn screening in order to early prevent structural lung damage.

The dose of TG2 inhibitor and of potentiator will be adapted to the specific situation taking into account patient's age, general health conditions, weight, other concomitant therapies and responsiveness to the combined treatment over time.

Another embodiment is a pharmaceutical composition containing a TG2 inhibitor and/or a ROS inhibitor and/or a potentiator as above defined, for use in a method for the treatment of ΔF508 cystic fibrosis according to the present invention. The composition is in a suitable pharmaceutical form for oral, aerosolized or parenteral administration and contains an effective amount of active ingredients together with pharmaceutically acceptable excipients.

The invention is further illustrated by the following examples and the annexed Figures.

DESCRIPTION OF THE FIGURES

(A, B) Freshly isolated brushed nasal epithelial cells from 5 ΔF508-CFTR homozygous patients were incubated for 18 h with medium or Vrx-325, Corr-4a, cystamine or EUK-134, washed and then kept with medium alone for 24 h. Brushed nasal epithelial cells from 5 non-CF controls were cultured with medium alone (WT/WT: medium). Assessment of iodide efflux by a fluorescence assay (SPQ) upon stimulation with forskolin (Fsk) plus (A) genistein (Gen) or (B) Vrx-532. SPQ fluorescence intensity (a.u.) (top) and rate of chloride efflux (bottom) measured in at least 50 cells per experiment. Mean±SD of 3 experiments; *P<0.01 vs ΔF508/ΔF508 cultured with medium (ΔF508/ΔF508: medium); ANOVA.

(A, B) Nasal polyp biopsies from ΔF508 homozygous patients cultured for 18 h with medium, or cystamine, followed by 36 h of incubation with medium alone. (A) Confocal images of CFTR. Data representative of five patients. Scale bar 10 μm. (B) Confocal images of in situ detection of TG2 activity and phospho-tyrosine (anti-PY-99 Ab). Data representative of five patients. Scale bar 10 μm. (C) Left, nasal polyp biopsies from ΔF508/ΔF508 patients (n=5) pulsed for 30 min with medium or genistein (Gen) followed by 4 h of PA-LPS challenge. Right, pulses of 30 min with genistein (Gen) followed by 4 h of PA-LPS challenge in nasal polyp biopsies from ΔF508/ΔF508 patients (n=5) pre-treated with cystamine for 18 h, then washed and kept in medium alone for 24 h. Confocal microscopy images of phospho-tyrosine (anti-PY-99 Ab). At least 30 fields were randomly sampled on three slides from each patient. Scale bar, 10 μm.

(A, B) Cftr$^{F508del}$ mice were treated intraperitoneally (i.p.) for 7 days with PBS or cystamine followed by 10 days of PBS (n=7 mice per each group of treatment). (A) Confocal microscopy images of CFTR (clone H182). (B) quantitative PCR analysis of TNF-α expression levels in lung homogenates (left), ELISA detection of MIP-2 protein levels in lung homogenates (middle) and number of CD68+ macrophages (per mm² of lung tissue) counted in 15-20 different random selected fields per lung per mouse for each experimental group (right). *P<0.05,  P<0.01, *P<0.001 compared to PBS treated mice (ANOVA). (C) $Cftr^{F508del}$ mice (n=5 mice per group of treatment) treated with aerosolized cystamine or vehicle for 7 days followed by aerosolized PBS for 10 days and then pulsed once with intraperitoneal genistein (Gen) followed by aerosolized PA-LPS challenge. TNF-α expression and CD68− macrophages counts measured as in (B). Data represent two pooled experiments (n=5 mice per group). #P<0.05, ##P<0.01, vs PBS treated mice, respectively; §P<0.05; ANOVA.

EXAMPLE 1—

Figure 1:
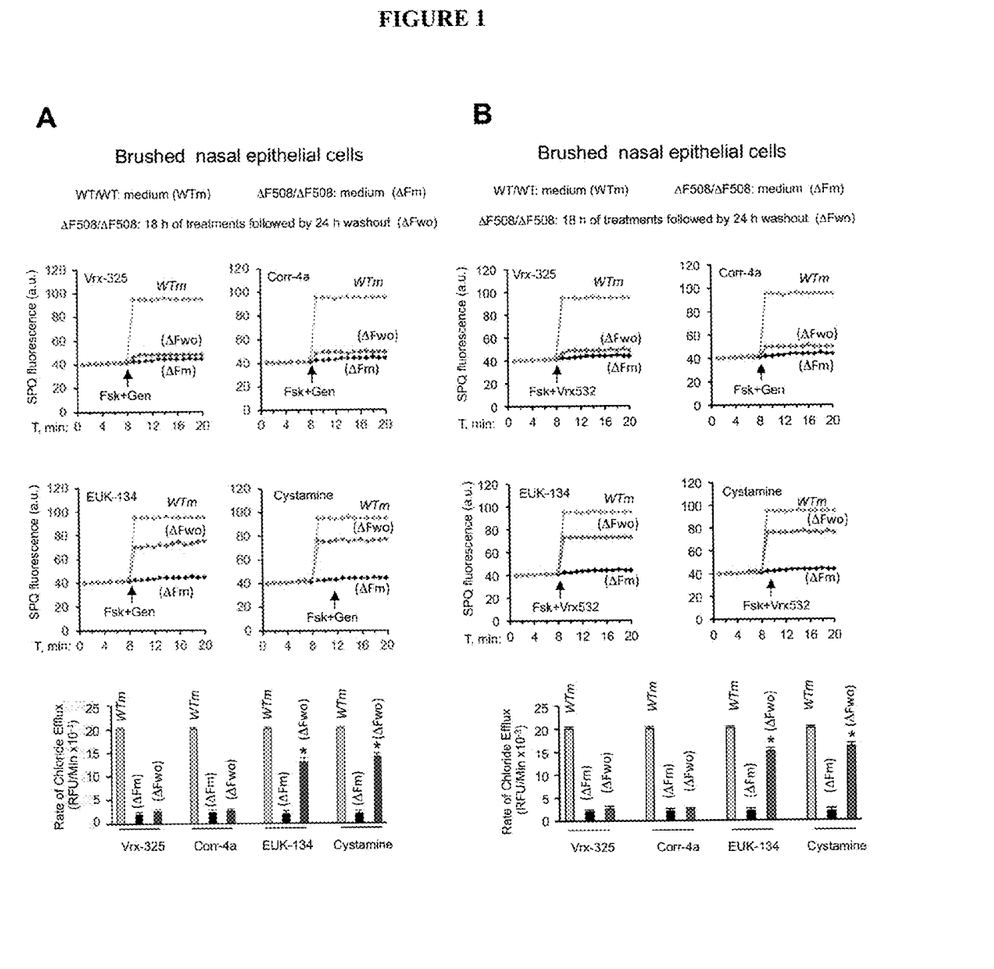
FIG. 1. Cystamine and EUK-134 sustain ΔF508-CFTR channel function beyond drug washout and enable the action of the potentiators genistein or Vrx-532 in freshly isolated brushed nasal epithelial cells from ΔF508-CFTR homozygous CF patients.

Cystamine and Antioxidants Induce and Sustain Channel Function of Rescued ΔF508-CFTR in Primary Brushed Nasal Epithelial Cells from ΔF508/ΔF508 Patients We examined whether cystamine or EUK-134 (Luciani A, 2010) would induce and sustain functional ΔF508-CFTR expression in freshly isolated brushed nasal epithelial cells from ΔF508/ΔF508 patients (Table 1A). We used primary nasal epithelial cells freshly obtained from ΔF508-CFTR homozygous patients, to directly test the efficacy of these autophagy-rescuing strategies on CFTR function in human airways. We used a fluorescent-based SPQ halide efflux assays (Silvis M R, 2009) to test the response to a short pulse of forskolin (FSK) added together with either of two different CFTR potentiators, genistein or VX-532, (Van Goor F, 2010) and analyzed at least 50 brushed nasal cells for group of treatment in each patient. Freshly isolated brushed nasal epithelial cells were incubated for 18 h with either cystamine or EUK-134 or with the well known CFTR correctors Corr-4a and VRT-325. SPQ halide efflux assays revealed that in contrast to Corr-4a and VRT-325, which only had scarce effects, transient exposure (18 h, followed by wash and reculture for 24 h with medium) to cystamine and EUK-134 rendered the cells capable of conserving ΔF508-CFTR response to a short pulse of forskolin (FSK) added together with either of two CFTR potentiators, genistein or VX-532 (FIG. 1).

Methods

Human Samples: Brushed Nasal Epithelial Cell.

Nasal epithelial cells freshly isolated by nasal brushing from 5 CF patients carrying ΔF508/ΔF508 CFTR mutations (see Table 1A) and 5 non-CF age- and sex-matched controls (3 F, mean age 12.5 yrs) were immersed in washing solution (PBS, DTT 2 mM, EDTA 10 mM) at 37° C. for 1 h on thermal shaker, centrifuged at 2,300×g for 20 min and washed in PBS. The isolated cells were maintained in 1 ml MEM Earl's salt L-Glutamine medium supplemented with 10% FBS and the appropriate amount of penicillin/streptomycin.[31] Brushed nasal cells were cultured for 18 h with medium, Vrx-325, Corr-4a (10 μM up to 50 μM) (kindly provided by Cystic Fibrosis Foundation, USA), cystamine (250 μM, Sigma-Aldrich), EUK-134 (50 μg ml⁻¹, Vinci Biochem), followed by 24 h of incubation with medium alone.

Informed consent was obtained from all subjects and the ethical committee of the University of Naples Federico II approved the study (N° 290/09).

TABLE 1A

Clinical characteristics of Cystic Fibrosis patients

| Patients # | 1 | 2 | 3 | 4 | 5 |
|---|---|---|---|---|---|
| Sex; | F | M | F | M | F |
| Age* | 11, 2 | 13, 2 | 12 | 15 | 10, 1 |
| Age at diagnosis* | 1, 2 | 0, 9 | 2, 4 | 0, 8 | 1, 6 |

| | Genotype | | | | |
|---|---|---|---|---|---|
| | ΔF508/ ΔF508 | ΔF508/ ΔF508 | ΔF508/ ΔF508 | ΔF508/ ΔF508 | ΔF508/ ΔF508 |
| Pancreatic insufficiency | Yes | Yes | Yes | Yes | Yes |
| Chronic respiratory infection (PA) | Yes | No | Yes | Yes | No |
| Mean FEV1, % predicted | 78 | 72 | 73 | 69 | 70 | patient's number
*(years, months)

Iodide efflux. The iodide-sensitive fluorescent indicator, SPQ (Molecular Probes, Eugene, Oreg.) (Silvis M R, 2009) was introduced into cells in a hypotonic solution of iodide buffer (in mM: 130 NaI, 4 KNO₃, 1 Ca(NO₃)₂, 1 Mg(NO₃)₂, 10 glucose and 20 HEPES, pH 7.4) diluted 1:1 with water and containing a final concentration of 10 μM SPQ. Cells were loaded for 20 min at 37° C. in a humidified chamber with 5% CO2. The SPQ-loaded cells were then mounted on a LSM510 Meta confocal microscope with a 37° C. heated stage and perfused with iodide buffer. Changes in CFTR-mediated SPQ fluorescence were monitored at the 445 nm wavelength in response to excitation at 340 nm during perfusion at 37° C. in nitrate buffer (NaI replaced with 130 mM NaNO₃) for 10 min with 20 μM forskolin plus 50 μM genistein or 20 μM forskolin plus 20 μM VRX-532 (kindly provided by Cystic Fibrosis Foundation, USA). The peak iodide efflux rate (usually 12 min after forskolin plus genistein or forskolin plus Vrx-532) of treated or untreated cells was calculated in accordance with the Stern-Volmer relationship as follows:

$$(F_o/F)-1=KC_Q$$

where F is the observed fluorescence, $F_o$ is the fluorescence in the absence of a quenching anion, $C_Q$ is the concentration of the quenching anion, and K is the Stern-Volmer quench constant. The rates were calculated using SigmaPlot Version 7.1 for each mean fluorescence trace generated from the 50 cells examined per population per coverslip.

Statistical analysis. Data are reported as arithmetic mean±SD. Data distribution was analyzed for normality and statistical analysis performed using the one-way ANOVA. Significant differences are indicated in the figures. All data were obtained from independent measurements. Data were analyzed using SPSS 13 software. Statistical significance was defined as P value of <0.05.

EXAMPLE 2—

Cystamine Re-Establishes ΔF508-CFTR Expression in Human Nasal Polyp Mucosae from CF Patients To translate these findings to human CF airways, we used an ex-vivo model of cultured nasal polyp biopsies belonging to CF patients, a useful tool to test potential strategies of modulation of mucosal response to environmental triggers within their natural environment (Raia V, 2005, Maiuri L, 2008).

Figure 2:
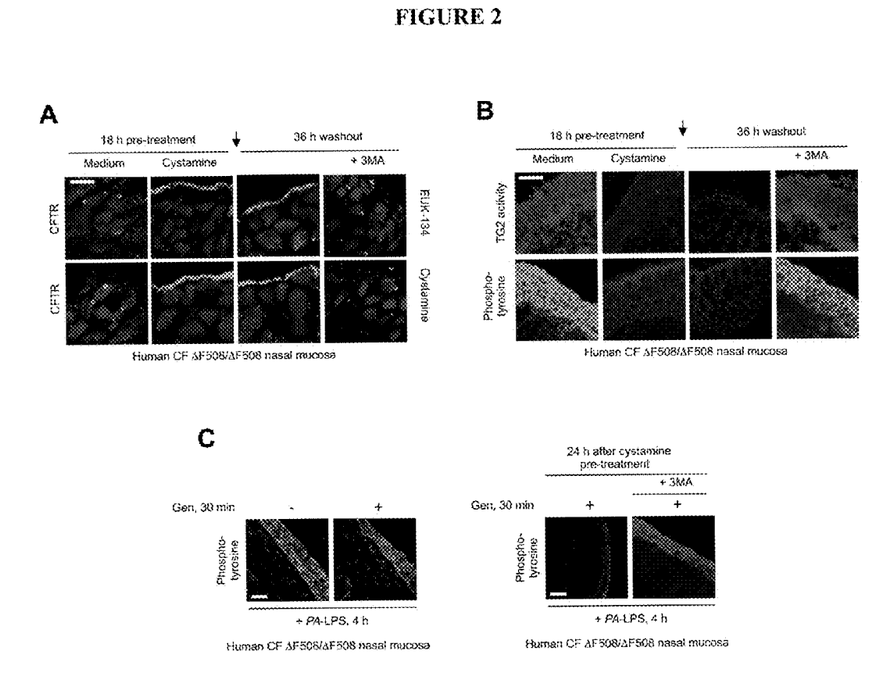
FIG. 2. Prior incubation with cystamine sustains ΔF508-CFTR at the airway epithelial surface and enables the activity of Genistein in controlling either constitutive or LPS-induced signs of inflammation beyond cystamine washout in nasal mucosa from ΔF508-CFTR homozygous CF patients.

Nasal polyp biopsies from five ΔF508/ΔF508 patients (Table 1B) were treated with cystamine for 18 h, washed and then cultured for further 36 h in the absence of cystamine. Confocal microscopy revealed that cystamine-mediated rescue of CFTR at the epithelial surface persisted for 36 h after cystamine withdrawal. Moreover, the reduction of signs of mucosal inflammation induced by cystamine, as TG2 activitation and protein tyrosine phosphorylation, persisted after 36 h of washout (FIG. 2).

Next, ΔF508/ΔF508 nasal polyp biopsies were pulsed for 30 min with genistein followed by 4 h incubation with PA-LPS. Genistein was not effective in reducing epithelial protein phosphorylation. To examine whether pre-treatment with cystamine was effective in enabling the action of genistein in human airways, nasal polyp biopsies were incubated with cystamine or medium for 18 h, then washed and kept in medium alone for 24 h and finally pulsed for 30 min with genistein followed by 4 h PA-LPS. In this experimental setting a synergistic effect of sequential treatment with cystamine plus genistein was observed (FIG. 2).

Our results indicate that in our system genistein has no effect on its own, but instead potentiates the activity of ΔF508-CFTR which is still resident at the epithelial surface well beyond washout after cystamine pre-treatment.

Methods

Human samples: ex vivo cultures of nasal polyp mucosal biopsies. Nasal polyp biopsies from 5 ΔF508 homozygous patients undergoing surgical treatment for non-allergic nasal polyposis (see Table 1B) were cultured as previously described,[7,19,32] for 18 h with medium, cystamine or EUK-134, followed by 36 h of incubation with medium alone, and then pulsed for 30 min with medium or genistein followed by 4 h of PA-LPS challenge.

Informed consent was obtained from all subjects and the ethical committee of the University of Naples Federico II approved the study (N° 290/09).

TABLE 1B

Clinical characteristics of Cystic Fibrosis patients

| Patients # | 1 | 2 | 3 | 4 | 5 |
|---|---|---|---|---|---|
| Sex; | F | F | M | M | M |
| Age* | 13, 5 | 12, 7 | 13, 3 | 11, 8 | 9, 7 |
| Age at diagnosis* | 0, 5 | 6, 3 | 1, 6 | 0, 4 | 0, 6 |

| | Genotype | | | | |
|---|---|---|---|---|---|
| | ΔF508/ ΔF508 | ΔF508/ ΔF508 | ΔF508/ ΔF508 | ΔF508/ ΔF508 | ΔF508/ ΔF508 |
| Pancreatic insufficiency | Yes | Yes | Yes | Yes | Yes |
| Chronic respiratory infection (PA) | Yes | No | Yes | Yes | Yes |
| Mean FEV1, % predicted | 72 | 68 | 80 | 74 | 83 | patient's number
*(years, months)

Immunofluorescence and Confocal microscopy. The procedures were performed as previously described.

Human tissue sections: five-micrometer frozen human lung tissue sections were fixed in acetone for 10 min. The sections were incubated for 2 h at room temperature with the indicated antibodies (Abs). The sections were incubated for 2 h at room temperature with the primary Abs. The primary Abs were: CFTR 1:100 (CF3, Abcam), CFTR 1:100 (H-182, Santa Cruz Biotecnology) (used on mouse tissue), phospho-Tyr 1:200 (Santa Cruz Biotecnology), p62 1:300 (Sigma). These were followed by incubation with Alexa 488 or 546 secondary antibodies (Molecular Probe, Invitrogen). Data were analyzed under fluorescence examination by a LSM510 Zeiss confocal laser-scanning unit (Carl Zeiss, Germany).

In situ detection of TG2 exzyme activity. TG2 activity in tissue samples was detected by incubating unfixed sections with biotinylated monodansylcadaverine for 1 h at 37° C. The incorporation of labeled substrate was visualized by incubation with Alexa 546-conjugated streptavidin (1:100; Molecular Probes, Invitrogen) for 30 min.

Statistical analysis. Data are reported as arithmetic mean±SD. Data distribution was analyzed for normality and statistical analysis performed using the one-way ANOVA. Significant differences are indicated in the figures. All data were obtained from independent measurements. Data were analyzed using SPSS 13 software. Statistical significance was defined as P value of <0.05.

EXAMPLE 3—

Figure 3:
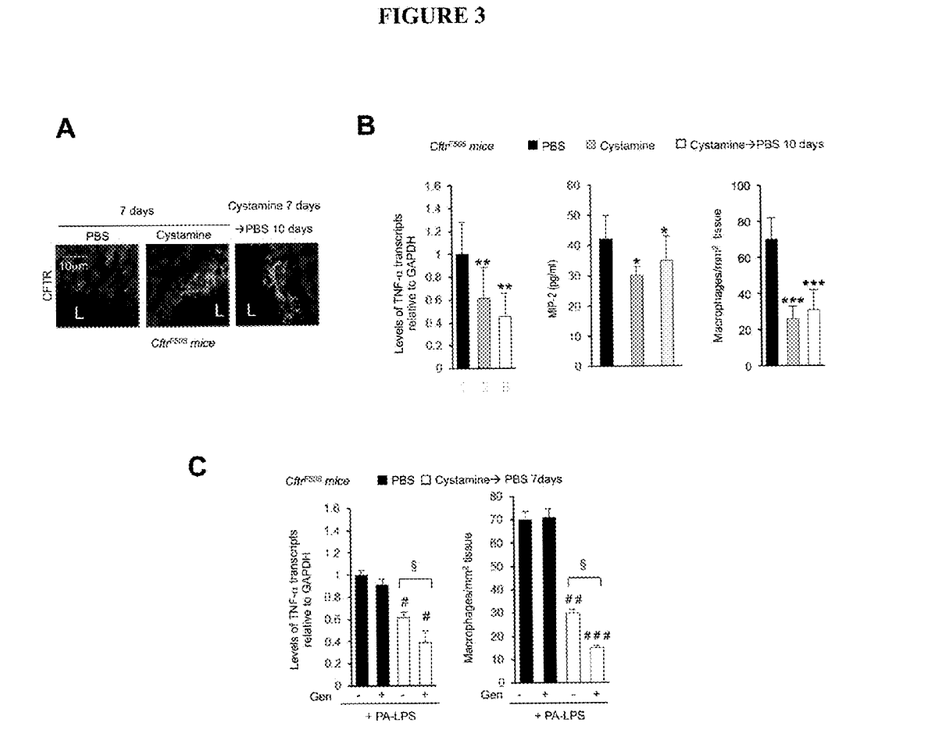
FIG. 3. Prior treatment with cystamine enables the activity of Genistein in controlling lung inflammation in Cftr$^{F508del}$ homozygous mice beyond cystamine washout.

Cystamine Re-Establishes Functional ΔF508-CFTR Expression in $Cftr^{F508del}$ Mice and Ensures Prolonged Control of Lung Inflammation Well Beyond Drug Washout Here we examined whether prior pharmacological restoration of autophagy by cystamine could abrogate the reported lack of efficacy of CFTR potentiators in vivo on ΔF508-CFTR homozygous airways. First, to test whether cystamine could prolong the expression of ΔF508-CFTR at the lung epithelial surface beyond drug washout, $Cftr^{F508del}$ mice were administered intraperitoneally (i.p.) for 7 days with vehicle alone or cystamine, a regimen that can ameliorate lung inflammation in vivo, or with cystamine (7 days) followed by 10 days of vehicle only. In this experimental model, the effects of cystamine in sustaining the re-location of ΔF508 protein at the respiratory epithelial surface and in reducing lung inflammation, persisted for 10 days after cystamine withdrawal and were abrogated by intraperitoneal treatment with 3-MA during the phase of withdrawal. (FIG. 3)

Next, we wondered whether these prolonged effects of cystamine could enable the beneficial action of potentiators on ΔF508-CFTR homozygous airways. To address this hypothesis, another group of 5 $Cftr^{F508del}$ treated with daily inhalations of aerosolized cystamine (0.2 mg/mouse/day) for one week, a regimen that reduced lung inflammation, kept for another week without treatment, and then sequentially pulsed with genistein and aerosolized PA-LPS, as above detailed. Genistein further improved the effects of cystamine pre-treatment and hence significantly reduced the signs of lung inflammation, but had no effect on its own, in mice that had not been pretreated with cystamine (FIG. 3). Cystamine and genistein were both not effective in wt littermates. These results indicate that prior restablishment of proteostasis and restoration of autophagy can create the conditions in which CFTR potentiators become capable of alleviating lung inflammation.

Methods

Mice and treatments. CF mice homozygous for the ΔF508-CFTR mutation (abbreviated $Cftr^{F508del}$)[7,29,30] in the 129/FVB outbred background (Cftrtm1EUR, F508del, FVB/129) were used.

These studies and procedures were approved by the local Ethics Committee for Animal Welfare (IACUC N° 382) and conformed to the European Community regulations for animal use in research (CEE no. 86/609). Anaesthetized $Cftr^{F508del}$ homozygous mice were treated with daily intraperitoneal injections of cystamine (100 µl of 0.01 M in PBS) or PBS for 7 days or with cystamine (7 days) followed by 10 days of PBS alone (n=7 mice per group). Other groups of Cftr$^{F508del}$ mice were treated by either intraperitoneal administration or inhalation of nebulized cystamine (0.2 mg\mouse\day) or vehicle for one week and 7 days following cystamine withdrawal were pulsed with a single intraperitoneal administration of genistein (50 mg kg−1) followed by a challenge with aerosolized PA-LPS (10 µg/20 g body weight) (n=7 mice per group).

Real-Time and Reverse-Transcription PCR Analysis. Total RNA was extracted with the RNeasy Mini Kit (Qiagen). The mRNA was reverse transcribed with a SuperScript™ III First Strand Synthesis System (Invitrogen). Quantitative RT-PCR was performed with an iCycler iQ Multicolour Real-Time PCR Detector (Bio-Rad) with iQ TM SYBR Green supermix (Bio-Rad). Expression levels of genes were normalized to GAPDH levels in the same sample. The relative amounts of mRNA were calculated by using the comparative Ct method. Real-time RT-PCR analyses were executed for evaluating efficiency of TNF-α. The sequence of TNFα primers were: Forward: CCAC-CACGCTCTTCTGTCTA; Reverse: AGGGTCTGGGC-CATAGAACT.

ELISA. Mouse MIP-2 secretion was measured using the BD OptEIATM MIP-2 ELISA kit II (BD Biosciences). Values were normalized to $10^6$ cells; results are expressed as means±SD.

Determination of macrophage numbers. We prepared cryostat sections (5 µm) from lung tissues of Cftr$^{F508del}$ mice. We fixed section on glass slides with acetone, washed with PBS-Tween (0.2%) and then incubated overnight at 4° C. with a 1:50 dilution of monoclonal rat CD68 (Acris) in PBS. This was followed by incubation with Alexa-488-conjugated secondary antibodies (1:100, Molecular Probes) and DAPI (Invitrogen) nuclear counterstaining. We then examined them on an LSM 510 confocal microscope (Zeiss). The analysis of macrophage numbers was performed by Image J software and each data point is expressed as the mean±SD of triplicate of three independent experiments.

Immunofluorescence and Confocal microscopy. The procedures were performed as previously described (Luciani A, 2010).

Mice lung tissues: seven-micrometer frozen lung tissue sections from each mice were fixed in acetone for 10 min. The sections were incubated for 2 h at room temperature with the primary Abs. The primary Abs were: CFTR 1:100 (CF3, Abcam), CFTR 1:100 (H-182, Santa Cruz Biotecnology) (used on mouse tissue), phospho-Tyr 1:200 (Santa Cruz Biotecnology), p62 1:300 (Sigma). These were followed by incubation with Alexa 488 or 546 secondary antibodies (Molecular Probe, Invitrogen). Data were analyzed under fluorescence examination by a LSM510 Zeiss confocal laser-scanning unit (Carl Zeiss, Germany).

In situ detection of TG2 exzyme activity. TG2 activity in tissue samples was detected by incubating unfixed sections with biotinylated monodansylcadaverine for 1 h at 37° C. The incorporation of labeled substrate was visualized by incubation with Alexa 546-conjugated streptavidin (1:100; Molecular Probes, Invitrogen) for 30 min.

Immunoblot analysis. The protein of lung homogenates were obtained from treated and untreated mice and the amounts of proteins were determined by a Bio-Rad protein assay to ensure equal protein loading before Western blot analysis. Fifty micrograms of protein were loaded in each lane. Antibodies against p62, 1:1000 (Sigma), and αβ-tubulin, 1:1000 (Cell Signaling Technology) were used as primary antibodies. Densitometric analysis was performed with Image J software; each data point is expressed as a mean±SD of triplicate of three independent experiments.

REFERENCES

O'Sullivan B P, Freedman S D. Cystic fibrosis. Lancet 2009; 373: 189-04.

Rowe S M, Miller S, Sorscher E J. Cystic fibrosis. N Engl J Med 2005; 352:1992-01.

Accurso F J. Update in cystic fibrosis 2005. Am J Respir Crit CareMed 2006; 173:944-47.

Collins F S. Cystic fibrosis: molecular biology and therapeutic implications. Science 1992; 256:774-779.

Park H W, Nam J H, Kim J Y, Namkung W, Yoon J S, Lee J S et al. Dynamic regulation of CFTR bicarbonate permeability by [Cl-]i and its role in pancreatic bicarbonate secretion. Gastroenterology 2010; 139:620-631.

Okiyoneda T, Barrière H, Bagdany M, Rabeh W M, Du K, Hohfeld J, et al. Peripheral protein quality control removes unfolded CFTR from the plasma membrane. Science 2010; 329:805-10.

Ramsey B W, Davies J, McElvaney N G, Tullis E, Bell S C, Dřevínek P, et al. A CFTR potentiator in patients with cystic fibrosis and the G551D mutation. N Engl J Med. 2011; 365:1663-72.

Davids P B. Therapy for cystic fibrosis—the end of the beginning? N Engl J Med. 2011; 365:1734-5.

Lukacs G L, Verkman A S. CFTR: folding, misfolding and correcting the ΔF508 conformational defect Trends Mol Med 2012; 18:81-91.

Belcher C N, Vij N. Protein processing and inflammatory signaling in Cystic Fibrosis: challenges and therapeutic strategies. Current Mol Med 2010; 10:82-94.

Clancy J P, et al, Results of a phase IIa study of VX-809, an investigational CFTR corrector compound, in subjects with cystic fibrosis homozygous for the F508del-CFTR mutation. Thorax 2012; 67:12-8.

Elborn S. Fixing cystic fibrosis CFTR with correctors and potentiators. Off to a good start. Thorax 2012; 67:4-5.

Maiuri L, et al. Tissue transglutaminase activation modulates inflammation in cystic fibrosis via PPARgamma down-regulation. J Immunol. 2008; 180:7697-705.

Luciani A, al. SUMOylation of tissue transglutaminase as link between oxidative stress and inflammation. J Immunol. 2009; 183: 2775-84.

Luciani A, et al. Defective CFTR induces aggresome formation and lung inflammation in cystic fibrosis through ROS-mediated autophagy inhibition. Nat Cell Biol. 2010; 12: 863-75.

Luciani A, et al. Cystic fibrosis: a disorder with defective autophagy. Autophagy 2011; 7:104-6.

Abdulrahman B A, et al. Autophagy stimulation by rapamycin suppresses lung inflammation and infection by Burkholderia cenocepacia in a model of cystic fibrosis. Autophagy. 2011; 7:1359-70.

Varga K, et al., Biochem. J. 2008; 410, 555.

Silvis M R, et al. Rab11b regulates the apical recycling of the cystic fibrosis transmembrane conductance regulator in polarized intestinal epithelial cells. Mol Biol Cell. 2009; 20:2337-50.

Van Goor F et al. Rescue of ΔF508-CFTR trafficking and gating in human cystic fibrosis airway primary cultures by small molecules. AJP—Lung Physiol. 2006; 260: L1117-L1130.

Raia V, et al. Inhibition of p38 mitogen activated protein kinase controls airway inflammation in cystic fibrosis Thorax 2005; 60, 773-80.

The invention claimed is:

1. A method of treating cystic fibrosis in a patient in need thereof, the method comprising administering to the patient a pharmaceutical composition comprising a tissue transglutaminase TG2 inhibitor, a channel activator (potentiator) of cystic fibrosis transmembrane conductance regulator (CFTR), and a pharmaceutically acceptable excipient; wherein the patient has cystic fibrosis and a ΔF508-CFTR mutation.

2. The method of claim 1, wherein the tissue transglutaminase TG2 inhibitor is cystamine, cysteamine, lipoic acid, tiopronin, acetylcysteine, carboxymethylcysteine, erdosteine, moguisteine, mesna, or glutathione; and the channel activator (potentiator) of cystic fibrosis transmembrane conductance regulator (CFTR) is VX-532, VX-770, or genistein.

3. The method of claim 1, wherein the tissue transglutaminase TG2 inhibitor is cysteamine; and the channel activator (potentiator) of cystic fibrosis transmembrane conductance regulator (CFTR) is VX-532.

4. The method of claim 1, wherein the tissue transglutaminase TG2 inhibitor is cysteamine; and the channel activator (potentiator) of cystic fibrosis transmembrane conductance regulator (CFTR) is VX-770.

5. The method of claim 1, wherein the tissue transglutaminase TG2 inhibitor is cysteamine; and the channel activator (potentiator) of cystic fibrosis transmembrane conductance regulator (CFTR) is genistein.

6. The method of claim 1, wherein the tissue transglutaminase TG2 inhibitor is cystamine or cysteamine.

7. The method of claim 1, wherein the pharmaceutical composition further comprises a reactive oxygen species (ROS) inhibitor.

8. The method of claim 7, wherein the ROS inhibitor is ellagic acid, caffeic acid, cumaric acid, gallic acid, resveratrol, luthein, astaxhantin, or zheaxhantin.

9. The method of claim 1, wherein the pharmaceutical composition further comprises a therapeutically effective amount of quercetin, silybin, apigenin, catechin, epigallocatechin, antocyanidin, or a combination of two or more thereof.

10. The method of claim 1, wherein the pharmaceutical composition is in a form for oral, aerosolized, or parenteral administration.

11. A method of treating cystic fibrosis in a patient in need thereof, the method comprising administering to the patient a therapeutically effective amount of (a) a tissue transglutaminase TG2 inhibitor selected from the group consisting of cystamine, cysteamine, lipoic acid, tiopronin, acetylcysteine, carboxymethylcysteine, erdosteine, moguisteine, mesna, and glutathione, and (b) a channel activator (potentiator) of cystic fibrosis transmembrane conductance regulator (CFTR) selected from the group consisting of VX-532, VX-770, and genistein; wherein the patient has cystic fibrosis and a ΔF508-CFTR mutation.

12. The method of claim 11, wherein the tissue transglutaminase TG2 inhibitor is cysteamine; and the channel activator (potentiator) of cystic fibrosis transmembrane conductance regulator (CFTR) is VX-532.

13. The method of claim 11, wherein the tissue transglutaminase TG2 inhibitor is cysteamine; and the channel activator (potentiator) of cystic fibrosis transmembrane conductance regulator (CFTR) is VX-770.

14. The method of claim 11, wherein the tissue transglutaminase TG2 inhibitor is cysteamine; and the channel activator (potentiator) of cystic fibrosis transmembrane conductance regulator (CFTR) is genistein.

15. The method of claim 11, wherein the tissue transglutaminase TG2 inhibitor is cystamine or cysteamine.

16. The method of claim 11, further comprising administering a therapeutically effective amount of a reactive oxygen species (ROS) inhibitor.

17. The method of claim 16, wherein the ROS inhibitor is ellagic acid, caffeic acid, cumaric acid, gallic acid, resveratrol, luthein, astaxhantin, or zheaxhantin.

18. The method of claim 11, further comprising administering a therapeutically effective amount of quercetin, silybin, apigenin, catechin, epigallocatechin, antocyanidin, or a combination of two or more thereof.

19. The method of claim 11, wherein the tissue transglutaminase TG2 inhibitor and the channel activator (potentiator) of cystic fibrosis transmembrane conductance regulator (CFTR) are administered by an oral route, a respiratory route, or a parenteral route.

* * * * *